United States Patent
Chahal et al.

(10) Patent No.: US 11,041,855 B2
(45) Date of Patent: Jun. 22, 2021

(54) NON-SPECIFIC, WIRELESS DETECTION OF ELECTRICALLY OR MAGNETICALLY LABELED BACTERIA AND/OR VIRUS

(71) Applicant: BOARD OF TRUSTEES OF MICHIGAN STATE UNIVERSITY, East Lansing, MI (US)

(72) Inventors: Premjeet Chahal, Okemos, MI (US); Evangelyn C. Alocilja, East Lansing, MI (US); Saranraj Karuppuswami, East Lansing, MI (US); Leann Lerie Matta, Dewitt, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 0 days.

(21) Appl. No.: 16/978,312

(22) PCT Filed: Mar. 5, 2019

(86) PCT No.: PCT/US2019/020648
§ 371 (c)(1),
(2) Date: Sep. 4, 2020

(87) PCT Pub. No.: WO2019/173264
PCT Pub. Date: Sep. 12, 2019

(65) Prior Publication Data
US 2021/0003567 A1  Jan. 7, 2021

Related U.S. Application Data

(60) Provisional application No. 62/638,635, filed on Mar. 5, 2018.

(51) Int. Cl.
*G01N 33/543* (2006.01)
*G01N 33/04* (2006.01)
(Continued)

(52) U.S. Cl.
CPC ..... *G01N 33/54346* (2013.01); *G01N 27/127* (2013.01); *G01N 27/221* (2013.01);
(Continued)

(58) Field of Classification Search
CPC ........... G01N 33/54346; G01N 27/127; G01N 27/221; G01N 27/745; G01N 33/04; G01N 33/14
(Continued)

(56) References Cited

U.S. PATENT DOCUMENTS 5,238,810 A * 8/1993 Fujiwara .......... G01N 33/54326
435/5
6,203,996 B1 * 3/2001 Duffy ....................... C12N 1/02
435/40.51

(Continued)

OTHER PUBLICATIONS

Neu, T. R. et al, Journal of Biomaterials Applications 1990, 5, 107-133.*
(Continued)

*Primary Examiner* — Arlen Soderquist
(74) *Attorney, Agent, or Firm* — Marshall, Gerstein & Borun LLP (57) ABSTRACT

The disclosure relates to wireless detection of analytes (such as bacteria) labeled by electrically, dielectrically, or magnetically active nanoparticles, for example in quality control monitoring for food supply chain management. The disclosed apparatus includes a detection vessel or vial, a resonant sensor tag, an inductively coupled reader to induce and detect resonance in the sensor tag, and an active nanoparticle for labeling. The disclosed wireless detection apparatus and methods use active nanoparticles for the development of wireless sensor systems which can be designed to be compatible with the existing RFID technology infrastructure. For example, commercial RFID readers (e.g., hand-held) used for tracking and tracing operation can
(Continued)

be used with the disclosed apparatus to induce and measure a corresponding resonance frequency.

31 Claims, 5 Drawing Sheets

(51) Int. Cl.
  *G01N 33/14* (2006.01)
  *G01N 27/12* (2006.01)
  *G01N 27/22* (2006.01)
  *G01N 27/74* (2006.01)
(52) U.S. Cl.
  CPC .......... *G01N 27/745* (2013.01); *G01N 33/04* (2013.01); *G01N 33/14* (2013.01); *G01N 2333/245* (2013.01)
(58) Field of Classification Search
  USPC .......................................................... 436/63
  See application file for complete search history.

(56) References Cited

U.S. PATENT DOCUMENTS

| | | | | |
|---|---|---|---|---|
| 2001/0053535 | A1* | 12/2001 | Bashir | G01N 33/56911 435/34 |
| 2002/0119513 | A1* | 8/2002 | Alocilja | G01N 33/0031 435/34 |
| 2003/0153028 | A1* | 8/2003 | Refseth | C12Q 1/6834 435/34 |
| 2003/0153094 | A1* | 8/2003 | Alocilja | G01N 33/5438 436/516 |
| 2005/0059105 | A1* | 3/2005 | Alocilja | G01N 33/569 435/7.32 |
| 2007/0037225 | A1* | 2/2007 | Metzger | G01N 33/5438 435/7.22 |
| 2007/0069186 | A1* | 3/2007 | Alocilja | H01B 1/128 252/500 |
| 2007/0114181 | A1* | 5/2007 | Li | B82Y 15/00 210/695 |
| 2008/0314766 | A1* | 12/2008 | Alocilja | G01N 33/56916 205/777.5 |
| 2009/0123939 | A1* | 5/2009 | Alocilja | G01N 27/745 435/7.2 |
| 2009/0123988 | A1* | 5/2009 | Hollander | C12N 7/00 435/239 |
| 2009/0181441 | A1* | 7/2009 | Jin | G01N 33/544 435/180 |
| 2009/0273354 | A1* | 11/2009 | Dhirani | G01N 27/3278 324/663 |
| 2010/0062416 | A1* | 3/2010 | Bergwerff | G01N 33/54353 435/5 |
| 2010/0134286 | A1* | 6/2010 | Potyrailo | G06K 19/07749 340/572.1 |
| 2010/0188075 | A1* | 7/2010 | Litvinov | G01N 33/54373 324/214 |
| 2011/0171749 | A1* | 7/2011 | Alocilja | B82Y 15/00 436/501 |
| 2011/0183398 | A1* | 7/2011 | Dasaratha | G01N 33/54333 435/178 |
| 2012/0315623 | A1* | 12/2012 | Alocilja | B82Y 15/00 435/5 |
| 2012/0322064 | A1* | 12/2012 | Alocilja | C12Q 1/6825 435/6.11 |
| 2014/0024026 | A1* | 1/2014 | Alocilja | G01N 33/56911 435/6.11 |
| 2014/0224673 | A1* | 8/2014 | Alocilja | C12Q 1/6811 205/780.5 |
| 2014/0228227 | A1* | 8/2014 | Litvinov | G01R 33/1269 506/9 |
| 2014/0303012 | A1* | 10/2014 | Alocilja | G01N 27/327 506/9 |
| 2014/0322823 | A1* | 10/2014 | Alocilja | C23C 18/44 436/501 |
| 2015/0104783 | A1* | 4/2015 | Al Ahmad | G01N 33/487 435/5 |
| 2015/0168322 | A1* | 6/2015 | Alocilja | G01R 33/28 435/7.1 |
| 2016/0223484 | A1 | 8/2016 | Potyrailo et al. | |

OTHER PUBLICATIONS

Nagel, J. A. et al, Journal of Biomaterials Science, Polymer Edition 1996, 7, 769-780.*
Ong, K. G. et al, Biosensors & Bioelectronics 2001, 16, 305-312.*
Ong, K. G. et al, SPIE 2002, 4575, 150-159.*
Radke, S. M. et al, Biosensors & Bioelectronics 2005, 20, 1662-1667.*
Lakshmanan, R. S. et al, Sensors and Actuators B 2007, 126, 544-550.*
Pang, P. et al, Biosensors & Bioelectronics 2007, 23, 295-299.*
El-Boubbou, K. et al, Journal of the American Chemical Society 2007, 129, 13392-13393.*
Johnson, M. L. et al, Sensors and Actuators A 2008, 144, 38-47.*
Pal, S. et al, IEEE Sensors Journal 2008, 8, 647-654.*
Lin, H. et al, Sensors and Actuators B 2010, 147, 343-349.*
Li, S. et al, Biosensorsand Bioelectronics 2010, 26, 1313-1319.*
Anderson, M. J. et al, Journal of Nanoparticle Research 2011, 13, 2843-2851.*
Mannoor, M. S. et al, Nature Communications 2012, 3, paper 763, 8 pages and 13 pages of supplementary information.*
Potyrailo, R. A. et al, Journal of Agriculture and Food Chemistry 2012, 60, 8535-8543.*
Sanz, D. A. et al, Sensors and Actuators B 2013, 178, 26-33.*
Croux, D. et al, Physica Status Solidi A 2013, 210, 938-944.*
Nguyen, S. D. et al, Electronics Letters 2013, 49, 1588-1589.*
Jiang, J. et al, Sensors and Actuators B 2014, 193, 653-659.*
Lee, H.-J. et al, Biosensors and Bioelectronics 2014, 61, 448-459.*
Fernandes, A. C. et al, Sensors 2014, 14, 15496-15524.*
Yuan, M. et al, IEEE Sensors Journal 2015, 15, 4442-4450.*
Wang, Y. et al, IEEE Sensors Journal 2015, 15, 4692-4699.*
Vasiljevic, D. et al, INFOTEH-JAHORINA 2016, 15, 11-14.*
Otten, L. et al, Analyst 2016, 141, 4305-4312.*
Horikawa, S. et al, SPIE 2016, 9864. paper 98640H, 10 pages.*
Karuppuswami, S. et al, 2016 IEEE 66th Electronic Components and Technology Conference 2016, 2401-2407.*
Karuppuswami, S. et al, 2016 IEEE 66th Electronic Components and Technology Conference 2016, 2535-2540.*
Sheybani, R. et al, Biosensors and Bioelectronics 2017, 92, 425-433.*
Xu, G. et al, Sensors and Actuators B 2017, 246, 748-755.*
Karuppuswami, S. et al, IEEE Sensors Journal 2017, 17, 1706-1714.*
Beltrami, L. V. R. et al, Journal of Food Engineering 2017, 212, 18-28.*
Pyo, H. et al, Sensors 2017, 17, paper 2012, 8 pages.*
Lim, D. et al, Philippine Journal of Pathology 2017, 2, 47-49.*
Huang, Q.-A. et al, 2017 IEEE 12th International Conference on ASIC (ASICON) 2017, 1121-1124.*
Karuppuswami, IEEE Sensors Letters, 2018, 2, Paper 3500704, 4 pages.*
Matta, L. L. et al, Biosensorsand Bioelectronics 2018, 117, 781-793.*
Matta, L. L. et al, Journal of Food Protection 2018, 81, 1941-1949.*
International Application No. PCT/US19/20648, International Search Report and Written Opinion, dated May 17, 2019.
Karuppuswami et al., A wireless RFI compatible sensor tag using gold nanoparticle markers for pathogen detection in the liquid food supply chain, IEEE Sensors Letters, pp. 104 (Apr. 4, 2018).
Matta et al., AuNP-RF sensor: An innovative application of RF technology for sensing pathogens electrically in liquids (SPEL) within the food supply chain, Biosens. Bioelectron., 111:152-158 (Jul. 2018).

(56) References Cited

OTHER PUBLICATIONS

Wang et al., Gold nanoparticle-labeled biosensor for rapid and sensitive detection of bacterial pathogens, J. Biol. Eng., 9:16 (2015).
Xu et al., Characterizing pilus-mediated adhesion of biofilm-forming *E. coli* to chemically diverse surfaces using atomic force microscopy, Langmuir, 29(9):3000-11 (Mar. 2013).

* cited by examiner

NON-SPECIFIC, WIRELESS DETECTION OF ELECTRICALLY OR MAGNETICALLY LABELED BACTERIA AND/OR VIRUS

CROSS-REFERENCE TO RELATED APPLICATIONS

This is a National Stage of International Application No. PCT/US2019/020648, filed Mar. 5, 2019, which claims the benefit of U.S. Provisional Application No. 62/638,635 (filed Mar. 5, 2018), which are incorporated herein by reference in their entireties.

STATEMENT OF GOVERNMENT INTEREST

None.

BACKGROUND OF THE DISCLOSURE

Field of the Disclosure

The disclosure relates to wireless detection of analytes (such as bacteria) labeled by electrically, dielectrically, or magnetically active nanoparticles, for example in quality control monitoring for food supply chain management. The disclosed apparatus includes a detection vessel or vial, a resonant sensor tag, an inductively coupled reader to induce and detect resonance in the sensor tag, and an active nanoparticle for labeling.

Background

Quality control measurements in a food supply chain and a corresponding contamination-free food supply chain promote global health and wellbeing. There are numerous pathogens which may be water-borne or food-borne, leading to deadly outbreaks of diseases that need to be controlled and eliminated. There are also reported cases of pathogens affecting food post-processing due to cross-contamination, improper handling or packaging. There is a growing need for following sustainable practices across the supply chain to uphold established quality and safety standards.

Traditionally, radiofrequency identification (RFID) tags have been used for tracking and tracing applications along the supply chain. The RFID tags can be categorized into active (battery inclusive) or passive (battery exclusive), chip-enabled (microchip inclusive) or chipless (IC and associated electronics exclusive), and regular or harmonic (uses higher order harmonics for operation).

In the early 1900s, U.S. public health officials linked unhygienic processed cow's milk with an epidemic of infant death and disease. In Chicago, for example, nearly 1 in 5 babies died before their first birthday, mainly from diarrhea. By the late 1920s, laws in most municipalities mandated that cow's milk be processed under sanitary conditions (i.e. pasteurized). Unlike sterilization, pasteurization is not intended to kill all microorganisms in the food but rather reduce the number of viable pathogens so they are unlikely to cause disease. To verify its efficacy, time-consuming microbiological techniques (plating) are passed over in favor of monitoring the activity of alkaline phosphatase (AP) since this enzyme is inactivated at slightly higher time-temperature conditions than those required to kill most pathogens in milk. However, this does not directly measure bacterial counts but is instead used as a benchmark. Measuring AP with this fluorometric method can detect levels down to 0.003% (e.g., 3 gallons of raw milk in 100,000 gallons of pasteurized milk).

Today, the U.S. dairy industry is federally required to be monitored and treated for bacterial contamination. Excessive bacterial counts are often associated with mastitis, an immune response to bacterial infection that causes the cow's mammary gland to become inflamed. North American dairy farmers lose annually $2 billion due to mastitis and infections can account for a 3-4% decrease in milk yield.

Testing of the milk typically occurs at the processing plant before it is unloaded. During any consecutive six month period, at least four samples must be collected by a representative of a state regulatory agency in four separate months for both raw Grade A and Grade B milk, and checked against several standards including: bacterial counts, somatic cell counts, and antibiotics.

The methods for determining Grade A milk quality are well established, and are based on the somatic cell count (SCC) and the bacteria plate count (BPC). Generally a higher somatic cell count indicates poor animal health, while a high bacteria plate count indicates poor equipment sanitation and/or infection. The majority of somatic cells are leukocytes (white blood cells), which become present in increasing numbers in milk usually as an immune response to a mastitis-causing pathogen. Dairy farmers are financially rewarded for low herd SCCs and penalized for high values, because cell counts reflect the quality of the milk produced. Milk contracts often define several SCC 'thresholds' and any respective bonus for attaining them.

As established, these measurements are taken daily from the milk bulk tank and not from individual cows. This is because testing of individual animals at each milking would be expensive, but it also means that milk from a sick cow is diluted and averaged down by the healthy animals. The bulk tanks on very large dairy units can accommodate mastitic cows in the herd without those cows affecting the overall milk quality rating, but for small to average-sized herds, knowing which cows are infected becomes more of a concern. Being so, less than 1% of milk collected from farms ends up being discarded by the distributor/processor.

SUMMARY

In view of the foregoing, there exists a need for improved, faster methods of determining the content of bacteria and other pathogens or analytes in milk or other food sample matrices. The disclosure accordingly relates to a tool capable of detecting bacterial levels within a complex liquid, which can be done in real time without the need for long incubations. An object of the disclosure is to provide dairy farmers and distributors with a means to directly detect bacterial contamination in milk.

In an illustrative application of the disclosure, potentially contaminated milk is introduced to a detection vessel or vial (or smart vial) made from an acrylic polymer. The vial also contains a RFID compatible sensor tag with an interdigitated capacitor coupled to an inducer and an external pick-up coil. Altogether, the apparatus is extremely sensitive to capacitive loading. Bacteria present in the liquid are incubated (e.g., for about 30 minutes) to attach to the surface aided by the polymer used. The sample is washed followed by exposure to a concentration of dextrin-coated gold nanoparticles (GNPs) and incubated again (e.g., for about 30 minutes). A resulting resonance frequency shift of the inductor-capacitor tank is directly correlated with the number of GNPs that capacitively loads the strong electric field regions of the interdigitated capacitor. As the concentration of bacteria increases, a lower number of GNPs bind to the interior surface of the detection vial, leading to lower shift in resonance frequency. Hence, an inverse relationship exists between pathogen concentration and resonance frequency shift due to capacitive loading with conductive nanoparticles.

Representative components of the disclosed method and corresponding analytical system can include gold nanoparticle labels, a 3D-printed or otherwise formed detection vial, a sensor tag, and an RF interrogation system. Gold nanoparticles with a dextrin-based coating or capping agent can be used as the labels. The dextrin helps maintain a specified size distribution of gold nanoparticles and aids in non-specific binding to bacteria via electrostatic charge. Low-cost 3D-printing technology is useful in forming a detection vial with desirable binding dynamics between the polymer surface (e.g., an acrylic polymer) of the vial and sample bacteria loaded with dextrin-coated gold nanoparticles. The sensor tag can be in the form of an inductor-capacitor resonant tank having high a Q-factor with an operating frequency suitably in an FCC-approved spectrum. The sensor tag can be tailored specifically for gold nanoparticles (or other types of nanoparticles/metal materials thereof). The presence of the nanoparticles alter the impedance (e.g., resistance, inductance, or capacitance), leading to a shift in resonance frequency or change in received power as detected by the sensor tag. The sensor may be electrical or magnetic in nature. Binding of nanoparticles affect the electric or magnetic field of the sensor and this can be read using an RF interrogation system. An illustrative embodiment uses a passive wireless interdigitated sensor tag for pathogen detection. The system provides real-time detection of analyte, and the read out system can be made compatible with RFID systems.

In an aspect, the disclosure relates to a method for wireless, non-specific detection of electrically, dielectrically, or magnetically labeled analytes, the method comprising: providing a detection apparatus comprising: a vessel comprising a wall (e.g., relatively thick, self-supporting structure; or relatively thin film or other supported structure) defining an internal sample volume and an (opposing) external surface, wherein (i) the internal sample volume is adapted to receive a (liquid) sample containing or suspected of containing an analyte, and (ii) the wall is adapted to non-specifically bind with both the analyte and a capped nanoparticle label; and a resonant tag (e.g., an inductive-capacitive (LC) resonant tag or antenna), positioned at the external surface of the vessel, wherein the inductive resonant tag is adapted to (i) wirelessly receive an induced voltage from an inductively coupled reader (e.g., an induction current in the inductively coupled reader), and (ii) correspondingly resonate at a selected resonance frequency in the absence of an additional capacitive load; and adding a sample containing or suspected of containing the analyte to the internal sample volume of the vessel; incubating the sample for a time sufficient to non-specifically bind analyte present in the sample to the wall of the vessel; adding a capped nanoparticle label to the internal sample volume of the vessel, the capped nanoparticle label comprising: (i) one or more of high dielectric constant nanoparticles, electrically conductive nanoparticles and magnetic nanoparticles (e.g., electrically conductive nanoparticles, magnetic nanoparticles, high dielectric nanoparticles, nanoparticles that have two or more of the foregoing properties, and mixtures of the foregoing), and (ii) a capping agent on an outer surface of the nanoparticles (e.g., capping agent present as a layer on an outer surface of the nanoparticles in an amount sufficient to stabilize an aqueous suspension of the nanoparticles; where the capped nanoparticle label can be added to the vessel in the form of an aqueous suspension); incubating the capped nanoparticle label for a time sufficient to non-specifically bind the capped nanoparticle label to the wall of the vessel; and inducing resonance in the resonant tag with an inductively coupled reader (e.g., separate from and external to the detection apparatus) and measuring the corresponding resonance frequency of the resonant tag (e.g., with the inductively coupled reader).

In another aspect, the disclosure relates to a kit for wireless, non-specific detection electrically, dielectrically, or magnetically labeled analytes, the kit comprising: (a) a detection apparatus comprising: a vessel comprising a wall defining an internal sample volume and an (opposing) external surface, wherein (i) the internal sample volume is adapted to receive a (liquid) sample containing or suspected of containing an analyte, and (ii) the wall is adapted to non-specifically bind with both the analyte and a capped nanoparticle label; and an inductive resonant tag positioned at the external surface of the vessel, wherein the inductive resonant tag is adapted to (i) wirelessly receive an induced voltage from an inductively coupled reader, and (ii) correspondingly resonate at a selected resonance frequency in the absence of an additional capacitive load; (b) capped nanoparticle label; and (c) (optionally) an inductively coupled reader (e.g., providing a simple means for data analysis if a measured result is above a known, reference threshold value).

Non-specific binding between the vessel wall, analyte, and/or capped nanoparticle label can be due to electrostatic forces, ionic interactions, hydrogen bonding interactions, or other dipole-dipole interactions. Non-specific binding can result between one or more functional groups in the wall (internal surface) material, the nanoparticle capping agent, and/or the analyte, such as carbonyl, carboxylic acid, carboxylate, hydroxyl, amino, ester, and/or amide groups. Wall interactions with the analyte and capped nanoparticle label are generally free from covalent attachments and specific binding interactions, such as those resulting from antibody and DNA or other oligonucleotide probes capable of binding/recognizing a specific target analyte (e.g., specific bacterium species, virus, protein, etc.). In an embodiment, the vessel and/or wall are free from specific-binding members such as antibody and DNA or other oligonucleotide probes. In an alternative embodiment, the vessel and/or wall can include immobilized (e.g., wall-immobilized) specific-binding members such as antibody and DNA or other oligonucleotide probes for binding/recognizing a specific target analyte of interest. In a further alternative embodiment, the vessel, wall, or portion(s) thereof (e.g., interrogation or measurement portion of the vessel/wall) can include sufficient immobilized specific-binding members thereon and/or be otherwise blocked (e.g., with bovine serum albumin (BSA)) to limit or prevent non-specific binding between analyte present in the sample and the wall of the vessel, in which case specific binding interactions are the primary interactions for binding target analyte present in the sample to the vessel or wall.

The resonant tag or antenna is generally a passive tag with no internal or wired power source, whether a battery or otherwise. Resonance in the tag is interrogated using a reader (e.g., with a battery or other wired electrical power source) proximal to the tag (e.g., wireless induction without physical electrical connection). The "selected resonance frequency" corresponds to the resonance frequency corresponding to the structure of the resonant tag alone (e.g., as determined by conventional electrical engineering design principles, whether for an inductive-capacitive (LC) resonant tag (e.g., an LC tank circuit), antenna, or otherwise).

Incubation of the sample to non-specifically bind analyte present in the sample to the wall of the vessel can include electrostatic binding or otherwise as described above. Alternatively or additionally, incubation of the sample to specifically bind analyte present in the sample to wall-immobilized specific-binding members such as antibody and DNA or other oligonucleotide probes can include specific binding interactions as described above for various alternative embodiments. Accordingly, in an embodiment, the vessel further comprises an immobilized specific binding member adapted to specifically bind a specific target analyte; and incubating the sample the sample further comprises specifically binding target analyte present in the sample to the specific binding member. The incubation time for non-specific and/or specific binding can be any suitable time such as at least 1, 2, 5, 10, 15, 30, or 60 minutes and/or up to 5, 10, 20, 30, 45, 60, 120, or 240 minutes, for example about 30 minutes. The incubation temperature can be any suitable temperature such as at least 10, 15, 20, or 25° C. and/or up to 20, 25, 30, 40, 60, or 80° C., for example about room temperature or 20-30° C.

Incubation of the capped nanoparticle label to non-specifically bind the capped nanoparticle label to the wall of the vessel can include binding or otherwise as described above. The incubation time can be any suitable time such as at least 1, 2, 5, 10, 15, 30, or 60 minutes and/or up to 5, 10, 20, 30, 45, 60, 120, or 240 minutes, for example about 30 minutes. The incubation temperature can be any suitable temperature such as at least 10, 15, 20, or 25° C. and/or up to 20, 25, 30, 40, 60, or 80° C., for example about room temperature or 20-30° C. Non-specific binding between the capped nanoparticle label and the vessel wall can occur to the extent that open wall surface area exists at point of addition. In cases where the original sample contains a large amount of analyte, the wall could be essentially entirely covered with non-specifically bound analyte and non-analyte components of the sample (e.g., proteins, fats, or carbohydrates as milk components), and essentially no capped nanoparticle label non-specifically binds to the vessel wall, even though the vessel containing the capped nanoparticle label was incubated under conditions sufficient to non-specifically bind, had wall surface area been available. Non-specific binding between the capped nanoparticle label and the analyte (e.g., bacteria or otherwise) can occur, although the effect of such binding on a resonance frequency shift is substantially less than the effect of capped nanoparticle label bound directly to the wall).

Measurement of resonance frequency, phase change, change in power (e.g., power consumed by the resonant tag), and/or quality-factor (Q-factor) can be used for a qualitative or quantitative determination regarding the presence or absence of the analyte in the original sample, for example based on a shift in resonance frequency between the sample resonance frequency and a reference resonance frequency. Example determinations include: analyte is present in original sample, analyte is absent from original sample, analyte has a particular concentration in original sample, etc.

Various refinements of the disclosed methods, apparatus, and kits are possible.

In a refinement, the wall of the vessel comprises a material selected from the group consisting of a polymer plastic, ceramic, and glass.

In a refinement, the wall of the vessel comprises a polymer selected from the group consisting of acrylics (e.g., poly(methyl methacrylate) (PMMA)), polycarbonates, polyamides (e.g., nylons), polystyrenes, polyolefins (e.g., polyethylenes, polypropylenes), polyvinylchorides, polyesters (e.g., polyethylene terephthalate (PET)), polyurethanes, poly(acrylonitrile butadiene styrene) (ABS), copolymers thereof, and combinations thereof. Many thermoplastic materials are suitable, and the vessel wall variously can be formed from the foregoing materials, include an interior coating or film forming from the foregoing materials, etc.

In a refinement, the wall of the vessel has a thickness in a range from 0.025 mm to 10 mm. The thickness can be at least 0.025, 0.5, 0.1, 0.2, 0.5, 1, or 2 mm and/or up to 0.5, 1, 2, 5, or 10 mm. The wall thickness represents the spacing between the internal cell volume where the analyte and/or the capped nanoparticle label bind to the wall and the external surface where the resonant tag is located. The resonant tag is suitably designed such that the fringes of the electrical field induced in its capacitive element extend through the wall and into the internal cell volume. For example, for an interdigitated capacitor element in an inductive resonant tag with a given finger spacing, the ratio of wall thickness: finger spacing suitably is at least 1, 2, 5, or 10 and/or up to 10, 15, 20, or 50, although values outside these ranges are also possible in various embodiment.

In a refinement, the internal sample volume is in a range from 0.005 ml to 1000 ml. The internal sample volume can be a relatively small volume such as a plate well where sample is pipetted for analysis, or it can be a relatively large volume such as vial, jar, bottle, or other container where a sample is collected and stored from a source and eventually analyzed in the same container. Example volumes can be at least 0.005, 0.01, 0.02, 0.05, 0.1, 0.2, 0.5, 1, 2, 5, or 10 ml and/or up to 0.1, 0.2, 0.5, 1, 2, 5, 10, 20, 50, 100, 200, 500, or 1000 ml.

In a refinement, the vessel is in the form of a sealable container (vial, jar, bottle, or other container, such as with a removable/sealable cap or lid), and the resonant tag is mounted at an external surface of the sealable container (e.g., adhered thereto or integrally form therewith, such as directly on the external surface or as part of a (plastic or paper) label, packaging material, or other structure applied to the external surface).

In a refinement, the resonant tag comprises an inductive-capacitive (LC) resonant tag such as an LC tank (e.g., an inductor (L) and capacitor (C) structure). In a further refinement, the LC tank comprises an interdigitated capacitor element. The LC tank (or resonant tag more generally) can further include an external pick-up coil or other structure for wirelessly receiving electrical signal from the reader. The particular electronic structure serving as the inductive-capacitive (LC) resonant tag is not particularly limited. Other types of structures/circuits that can function as an inductive-capacitive (LC) resonant tag (or just resonant tag) can be designed using metamaterials, antennas, a capacitor with self-inductance, an inductor with self-capacitance, coiled wires, magnetoelastic materials, among others.

In a refinement, the resonant tag comprises a radio-frequency identification (RFID) tag (e.g., a passive RFID tag). This can further include an electronic chip for identification, data storage, and/or data processing, in addition to its function as a resonance detector for the disclosed analyte detection apparatus.

In a refinement, the selected resonance frequency of the inductive resonant tag is in a range from 1 MHz to 20 MHz (e.g., at least 1, 2, 5 or 10 MHz and/or up to 5, 10, 15, or 20

MHz). More generally, the frequency can be tuned to be in the range of any prescribed frequency dictated by a local regulatory body (e.g., Federal Communications Commission (FCC) in the United States) for RFID infrastructure. For an LC circuit, the selected resonance frequency can be determined by $f_o=1/(2\pi(LC)^{0.5}$, where L is the inductance in Henrys, C is the capacitance in Farads, and $f_o$ is the frequency in Hertz. Example resonance frequencies or frequency ranges that are representative and compatible with conventional RFID technology and associated readers include 120-150 kHz (LF), (about) 13.56 MHz (HF). Others are 433 MHz (UHF), 865-868 MHz, 902-928 MHz, 2450-5800 MHz (microwave), and 3.1-10 GHz (microwave) that can be used using an antenna design which is also an another form of resonant structure. Resonance frequencies outside the foregoing ranges also can be used, for example for electronic article surveillance- (EAS-) compatible resonant tags.

In a refinement, the sample comprises milk. Other types of possible sample materials include water (e.g., bottled water, drinking water), fruit and vegetable juices, energy/soft drinks, other beverages, oils (e.g., cooking oils such as vegetable oils, olive oils), buttermilk or yogurt, meats, etc. Solid or semi-solid materials to be tested can be diluted, extracted, or otherwise contacted with water or other liquid medium before addition to the sample volume.

In a refinement, the analyte comprises bacteria. The examples illustrate *E. coli* as a representative bacteria, but the method is generally non-selective and applicable to any bacteria that might be present in a sample. Specifically, generally any bacteria species are capable of non-specific binding to the vessel wall, which in turn limits the available wall surface area for capped nanoparticle label, which in turn affects the degree of measured resonance frequency shift. Accordingly, a frequency shift result can be correlated to a total bacteria content for a specific sample. General classes of analytes that could non-specifically bind to the vessel wall can include biological materials, such as bacteria, viruses, proteins, etc. Potential non-specific binding of natural/normal/intended components in a non-contaminated sample matrix (e.g., a bacteria-free milk control sample) makes it generally preferable to analyze a non-contaminated sample matrix as a control. Generally, a reference is utilized for validating the sensor results, which can be included within the same resonant tag or separately.

In a refinement, the method for analyte detection further comprises, after incubating the sample (e.g., and before adding the capped nanoparticle label) removing the sample from the internal sample volume of the vessel, leaving analyte originally present in the sample still in the internal sample volume of the vessel and bound to the wall of the vessel (e.g., decanting/discarding sample, followed by washing/rinsing the vessel with wash solution, such as phosphate-buffered saline (PBS) or other aqueous rinse fluid).

In a refinement, the capped nanoparticle label comprises electrically conductive nanoparticles. In a further refinement, the electrically conductive nanoparticles comprise a metal selected from the group consisting of gold, chromium, copper, zinc, nickel, cadmium, silver, cobalt, indium, germanium, tin, lead, arsenic, antimony, bismuth, chromium, molybdenum, manganese, iron, ruthenium, rhodium, palladium, osmium, iridium, platinum, alloys thereof, and combinations thereof.

In a refinement, the capped nanoparticle label comprises magnetic nanoparticles. In a further refinement, the magnetic nanoparticles comprise a metal or metal oxide selected from the group consisting of iron, cobalt, nickel, gadolinium, alloys thereof, and combinations thereof (e.g., iron or iron-containing alloy magnetic material, nickel or nickel-containing alloy magnetic material, magnetic iron oxide such as $Fe_3O_4$ or gamma $Fe_2O_3$).

In a refinement, the capped nanoparticle label comprises high dielectric constant nanoparticles. In a further refinement, the high dielectric constant nanoparticles comprise a material selected from the group consisting of conjugated polymers (e.g., conductive polymers such as polypyyrroles, polyanilines, polyphenylenes, polyacetylenes, polythiophenes), titanium oxides (e.g., titanium dioxide/titania, barium strontium titanate, barium zirconium titanate, barium titanate, barium tetratitante, lead titanate, lead zirconium titanate, lead lanthanum zirconium titanate; such as with or without other metals in addition to titanium and oxygen), microwave ferrite materials (e.g., magnesium/nickel/lithium ferrite, yttrium/aluminum garnet), alumina, ceria (cerium (IV) oxide), and combinations thereof. The high dielectric constant nanoparticles can be formed from materials having a dielectric constant of at least 7, 10, 20, 50, 100, 1000, or 10000 and/or up to 50, 100, 1000, 10000, or 100000. Dielectric constants outside the foregoing ranges also can be used.

In a refinement, the nanoparticles have a particle size ranging from 2 nm to 250 nm (e.g., a number-, weight-, or volume-average particle size). For example, the average size of the nanoparticle distribution can be at least 2, 5, 8, 10, 12, or nm and/or up to 8, 10, 12, 15, 20, 25, 30, 40, or 250 nm.

In a refinement, the capping agent comprises at least one of a carbohydrate, citric acid, and a citric acid derivative (e.g., citrate).

In a refinement, the capping agent comprises an oligosaccharide having 3 to 100 saccharide residues (e.g., for example at least 3, 5, 10, 15, 20, 25, 30, or 40 and/or up to 10, 20, 30, 40, 50, 60, 80, or 100 saccharide residues). Dextrin is a suitable example.

In a refinement, the capped nanoparticle label comprises gold nanoparticles and a dextrin capping agent.

In a refinement, the inductively coupled reader is a handheld reader. The inductively coupled reader generally can be any conventional device that inductively couples to the sensor tag. The reader can accept wireless data and include a readout display that shows the resonance frequency and phase of the sensor. The inductively coupled reader can be a vector network analyzer, a RFID reader (e.g., an active RFID reader, such as for a passive inductive resonant tag), a magnetic inductive coil (wires), or an impedance analyzer. The reader determines the resonant frequency and/or the quality factor of the resonant frequency. This measurement can be compared against a background-stored electrical property or against a reference resonant tag which undergoes similar conditions apart from interacting with nanoparticles.

In a refinement, the method for analyte detection further comprises determining a resonance frequency shift between the resonance frequency measured for the sample and a reference resonance frequency. The reference resonance frequency can be based on a control sample that is of the same type/sample matrix as the unknown sample, but which is known to be free of analyte, and which has been otherwise analyzed in the same manner as the unknown sample (e.g., incubation in the vessel of the control sample, followed by incubation in the vessel of added capped nanoparticle label, followed by measurement of the resonance frequency for the control sample). In a further refinement, the method for analyte detection further comprises determining that the analyte was not present in the sample (e.g., qualitative determination of absence, or a quantitative determination that the analyte was not present above a lower level of detection). In a further refinement, the method for analyte detection further comprises determining that the analyte was present in the sample (e.g., qualitative determination of presence, or a quantitative determination that the analyte was present at a particular level or concentration, for example based on a calibration curve from analysis of reference samples with known analyte levels). In a further refinement, the method for analyte detection further comprises determining whether the analyte was present in the sample (i.e., alternative inquiry for the foregoing two possibilities).

In another aspect, the disclosure relates to a method for supply chain safety management of a product, the method comprising: taking a sample of a product (e.g., food product such as milk) to be analyzed for the presence of an analyte; performing the method for analyte detection in any of the various disclosed embodiments to determine whether the analyte was present in the sample; combining the product with a bulk supply of other corresponding product, depending on whether the analyte was present in the sample (e.g., combining the tested (food) product (such as milk) with a bulk supply of corresponding (food) products (such as milk) from other sources and which have already been tested or otherwise determined to be safe/non-contaminated, whether by the disclosed method or other methods). For example, if the presence of the analyte is representative of a contaminated or unsafe product (e.g., bacteria present), then the product can be combined with the bulk supply of other corresponding safe product when the analyte is absent, and the product can be discarded or possibly decontaminated before combining with the bulk supply of other corresponding safe product when the analyte is present. This could be the case where the presence of bacteria in a food product is unsafe or otherwise undesirable. Conversely, if the presence of the analyte is representative of a clean or safe product, then the product can be combined with the bulk supply of other corresponding safe product when the analyte is present, and the product can be discarded or possibly remediated before combining with the bulk supply of other corresponding safe product when the analyte is absent. This could be the case where the presence (or certain amount) of bacteria in a food product desirable, such as in cultured foods like yogurt, cheese, etc.

While the disclosed apparatus, compounds, methods and compositions are susceptible of embodiments in various forms, specific embodiments of the disclosure are illustrated (and will hereafter be described) with the understanding that the disclosure is intended to be illustrative, and is not intended to limit the claims to the specific embodiments described and illustrated herein.

BRIEF DESCRIPTION OF THE DRAWINGS

For a more complete understanding of the disclosure, reference should be made to the following detailed description and accompanying drawings wherein.

DETAILED DESCRIPTION

The disclosure relates to wireless (e.g., radiofrequency (RF), microwave frequency, or otherwise) detection of analytes (e.g., pathogens such as bacteria or viruses) labeled by electrically, dielectrically, or magnetically active nanoparticles. Such detection of analytes can be used in quality control monitoring for food supply chain management. With the availability of low cost hand-held receivers capable of recording real-time data, wireless (e.g., RF) sensing provides a tool for addressing different supply chain issues, promoting public health, providing economic savings, and protecting business reputations for industries and communities. The disclosed wireless detection apparatus and methods use active nanoparticles for the development of wireless sensor systems which can be designed to be compatible with the existing RFID technology infrastructure. For example, commercial RFID readers (e.g., hand-held readers) used for tracking and tracing operation can be used with the disclosed apparatus to induce and measure a corresponding resonance frequency.

Using the electric or magnetic field of an RF or other inductive-capacitive (LC) resonant sensor tag, the target analyte can be detected by any means of electromagnetic detection including, but not limited to, invasive or non-invasive methods such as conductive, capacitive, or inductive probing. The detection method includes, but is not limited to, wired direct probing, wireless near-field or far-field interrogation, and hand-held interrogation methods. The methods and apparatus can be used for quality control applications in the food supply chain. Tailoring the electrostatic forces allows non-specific binding attachment of the nanoparticles onto a vessel or vial surface or to the analyte. Labeled pathogens with the active nanoparticles along a surface allows wireless detection of the target analytes.

The disclosed detection system includes a detection vessel or vial (e.g., a "smart" vial as variously described herein), a sensor tag (e.g., inductive-capacitive (LC) resonant tag), an inductively coupled reader/interrogation system to induce and detect resonance in the sensor tag (e.g., RFID reader/interrogation system), and an active nanoparticle for labeling. The developed sensor systems are applicable to monitoring of various food supply chains including but not limited to dairy, water, oil and beverage supply chains.

Active nanoparticle labeling: Surface chemistry plays a role in the binding dynamics of the analyte to the smart vial wall and nanoparticles to the analyte. The nanoparticles having (inherent) positive or negative charge are coated with bio-compatible materials such as dextrin (or other carbohydrates) by using the electrostatic forces between the charged nanoparticle and carbohydrate. This leads to an increase in free surface charge groups, which repel each other preventing coagulation (or agglomeration) of nanoparticles, and prevents lysing of pathogens. Also, tailoring the coating dynamics provides a method to label the pathogens with active nanoparticles. The increase in free surface charge due to coating the nanoparticle surface aids in the attachment of nanoparticles to pathogens or to the surface (or the walls) of the smart vial. Additionally, the smart vial surface charges can specifically be tailored to attract or repel the active nanoparticles by coating it with different polymers that have inherently opposite or same free surface charges.

Reader/interrogation system: The binding of the nanoparticles on the surface of the smart vial activates the sensor system. The nanoparticles affect the electric field or magnetic field of the sensor and this can be read out using the RFID or other reader/interrogation system. The read out signal is monitored in real time and used for instantaneous detection of target analyte(s) in food. The output signal can be near-field or far-field, time-based or frequency-based (harmonics and sub-harmonics), and can also be used for extracting other information such as the sample number, distance, received power, and identification of the tag. The read out system can be made compatible with RFID system enabling packaging surveillance applications.

Sensor tag: The sensor tag preferably is a form of inductor-capacitor resonant tank having high Q-factor with an operating frequency an approved spectrum (e.g., 915 MHz for RFID applications in North America, such as based on FCC regulation). The sensor tag is made specific to the active nanoparticle bound on the smart vial, whether electrical or magnetic nanoparticle. The electrical tags are designed such that, the presence of nanoparticles alter the impedance (e.g., resistance, inductance or capacitance) leading to shift in resonance frequency or change in received power. The magnetic tags are designed such that, the nanoparticles load the inductance of the tag or coupling between the tag and the interrogation coil.

Detection vessel (smart vial): The smart vial is designed based on the sensing approach using low cost 3D printing technology. The material selected for the vial wall also affects the binding dynamics of the pathogens and nanoparticles. Recent development in 3D printing technology allows using different polymers for printing the vials. This allows a higher degree of freedom in the choice of surface charges on the vial.

Specificity: The smart vial surface can be selectively charged by printing different polymer combinations or by spray coating with antibodies or DNA leading to patterning of the pathogen or nanoparticle attachment. These patterns can be made unique and can allow selective binding dynamics of the pathogens and nanoparticles.

Advantages of the disclosed apparatus and methods include: detection of non-specific bacteria load as low as 5 log CFU/ml (e.g., as demonstrated using *E. Coli* C3000); antibody free labeling of pathogens; tailored electrostatic forces to provide binding of pathogens to smart vial and labeling of nanoparticles to pathogen; non-contact, non-invasive sensing approach with simple data analysis; compatible with RFID infrastructure; simple read-out circuitry (hand-held smart device compatible); compatible with short and long range wireless sensing; compatible with different types of bacteria loads; field operable low cost sensor kit; sensor tag compatible with roll to roll printing; compatible for detection within liquid food matrices such as milk, oil, juice, and beverages; compatible to detect different species of bacteria by using antibody or DNA coating if desired.

FIGS. 1-5 illustrate components of a detection apparatus 100 for wireless, non-specific detection of labeled analytes in a sample, as well as related system components and method steps for use of the detection apparatus 100.

Figure 1:
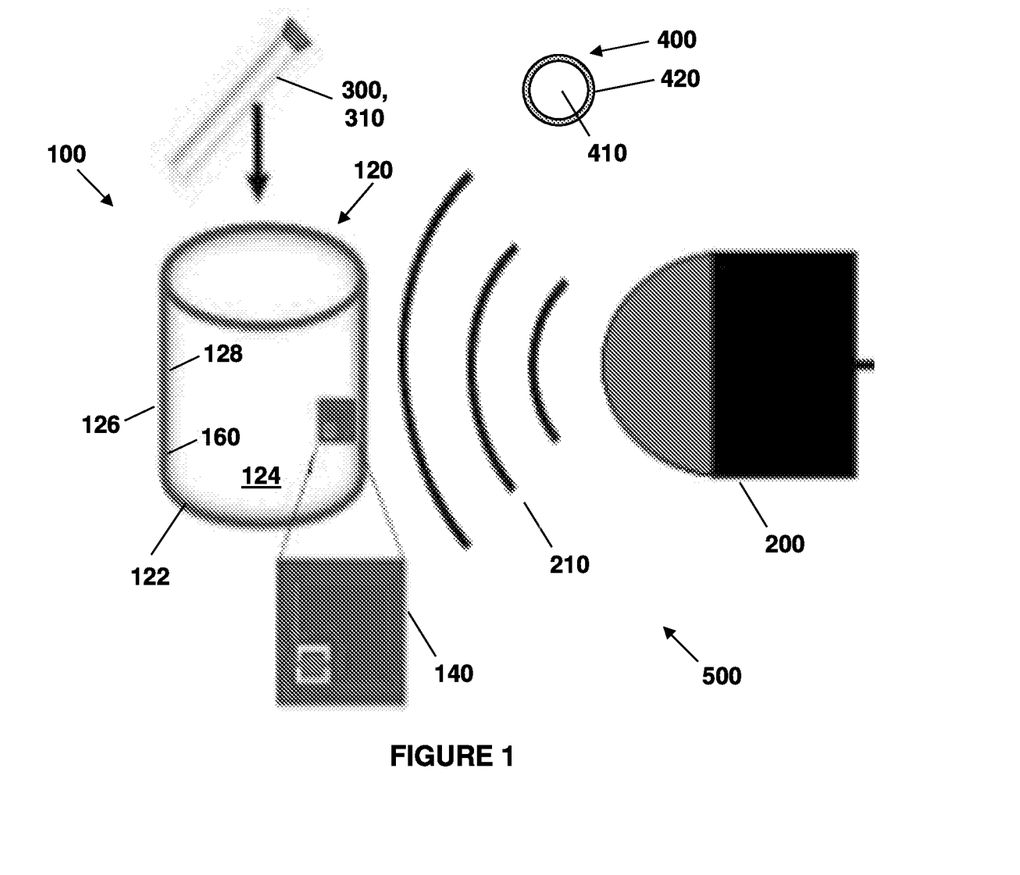
FIG. 1 illustrates a detection apparatus according to the disclosure along with a related system and method for detection of a labeled analyte.

The detection apparatus 100 generally includes a vessel 120 such as a vial or well for receiving a sample 300 to be analyzed as possibly containing an analyte 310 of interest, for example a milk or other food sample to be analyzed for the presence and/or concentration of bacteria or other pathogens. The vessel 120 includes a wall 122 or other surrounding structure that defines an internal sample or container volume 124 of the vessel 120. The wall 122 includes an internal surface 128 that is generally adjacent to the internal sample volume 124 and would be in contact with the sample 300 when present, and an external surface 126 that opposes the internal surface 128 and would not be in contact with the sample 300 when present (i.e., the outside of the container or vessel 120). The internal sample volume 124 is adapted to receive the sample 300 to be analyzed for the presence of the target analyte 310, for example having a sufficient volume to receive an aliquot of the sample 300 of desired sample size. The wall 122 and in particular the internal surface 128 thereof is adapted to non-specifically bind with both the analyte 310 and a capped nanoparticle label 400. Non-specific binding between the vessel wall 122, analyte 310, and/or capped nanoparticle label 400 can be due to electrostatic forces, ionic interactions, hydrogen bonding interactions, or other dipole-dipole interactions. Non-specific binding can result between one or more functional groups in the wall 122 (e.g., internal surface 128) material, the nanoparticle capping agent 420, and/or the analyte 310, such as carbonyl, carboxylic acid, carboxylate, hydroxyl, amino, ester, and/or amide groups. Examples of suitable materials for the wall 122 include polymer plastics, ceramics, and glass, in particular polymer materials including carbonyl, carboxylic acid, and/or carboxylate groups. In some embodiments, the vessel 120 further includes an immobilized specific binding member 160, for example on the internal surface 128, adapted to specifically bind a specific target analyte (e.g., an antibody or DNA probe adapted to specifically bind to a target bacteria, virus, or other pathogen). In other embodiments, the vessel 120, wall 122, and/or internal surface 128 thereof is free from specific binding members, immobilized or otherwise.

The detection apparatus 100 further includes a resonant tag 140 positioned at the external surface 126 of the vessel 120. The tag 140 can be mounted or bound to the surface 126, simply in contact with or adjacent to the surface 126, or otherwise near or proximal to the surface 126 (e.g., but not necessarily in contact therewith). The resonant tag 140 or antenna is generally a passive tag with no internal or wired power source, whether a battery or otherwise. Resonance in the tag 140 is interrogated using a reader (e.g., with a battery or other wired electrical power source) proximal to the tag 140 (e.g., wireless induction without physical electrical connection). Thus, the resonant tag 140 is adapted to wirelessly receive an RF field 210 and an induced voltage from an inductively coupled reader 200, and correspondingly resonate at a selected resonance frequency in the absence of an additional capacitive load. In some embodiments, the selected resonance frequency can be in a range from 1 kHz to 20 GHz, for example being at least 1, 2, 5, 10, 20, 50, or 100 kHz, at least 1, 2, 5, 10, 20, 50, or 100 MHz, up to 1, 2, 5, 10, 15, 20, 50, or 100 MHz, and/or up to 1, 2, 5, 10, or 20 GHz. The selected resonance frequency corresponds to the resonance frequency corresponding to the structure of the resonant tag 140 alone (e.g., as determined by conventional electrical engineering design principles, whether for an inductive-capacitive (LC) resonant tag (e.g., an LC tank circuit), antenna, or otherwise).

Figure 2:
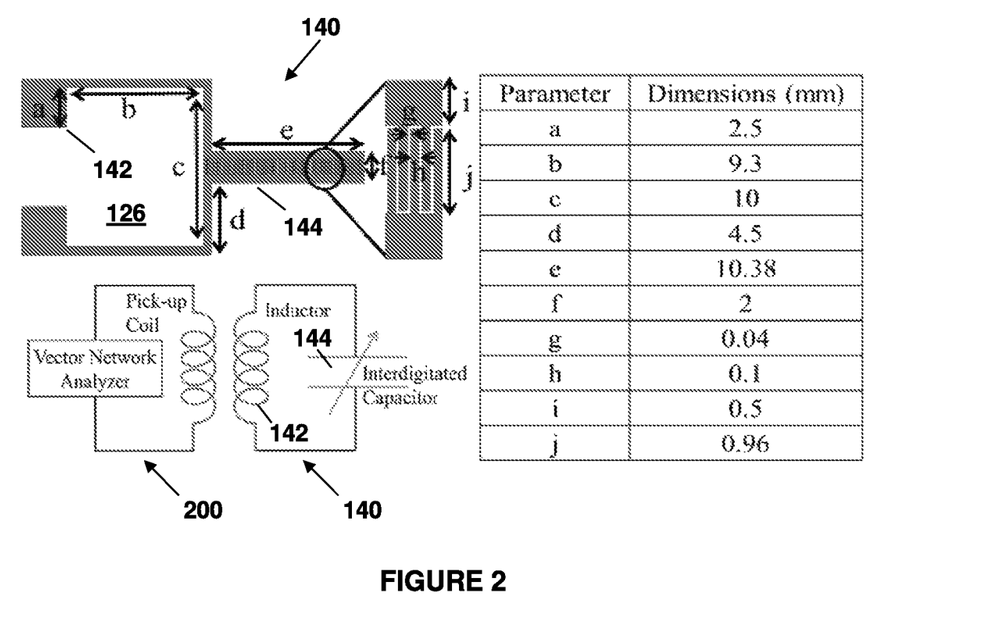
FIG. 2 illustrates a resonant tag according to the disclosure in the form of an LC tank.
Figure 3:
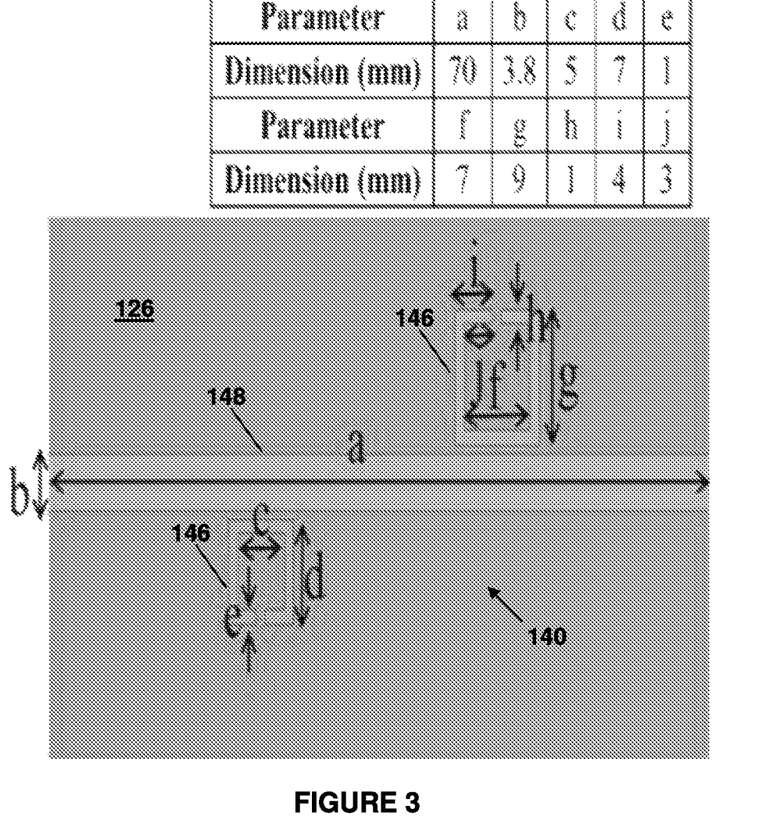
FIG. 3 illustrates a resonant tag according to the disclosure in the form of a split-ring resonance (SRR) tag.

The particular electronic structure serving as the resonant tag 140 is not particularly limited. In some embodiments, the resonant tag 140 can be an inductive-capacitive (LC) resonant tag 140 such as an LC tank, for example as illustrated in FIG. 2. The LC tank 140 includes an interdigitated capacitor 144 (C) coupled to an inductor 142 (L) and an external pick-up coil. In some embodiments, the resonant tag 140 can be a split ring resonant (SRR) tag 140, for example as illustrated in FIG. 3. The SRR tag 140 includes two square split rings 146 capacitively coupled to a transmission line 148, where one ring 146 can be used for measurement and the other ring can be used 146 for reference. Other types of structures/circuits that can function as an inductive-capacitive (LC) resonant tag 140 (or just resonant tag 140) can be designed using metamaterials, antennas, a capacitor with self-inductance, an inductor with self-capacitance, coiled wires, magnetoelastic materials, among others. In some embodiments, the resonant tag 140 includes a radio-frequency identification (RFID) tag (e.g., a passive RFID tag), which can further include an electronic chip for identification, data storage, and/or data processing, in addition to its function as a resonance detector for the detection apparatus 100.

Figure 5:
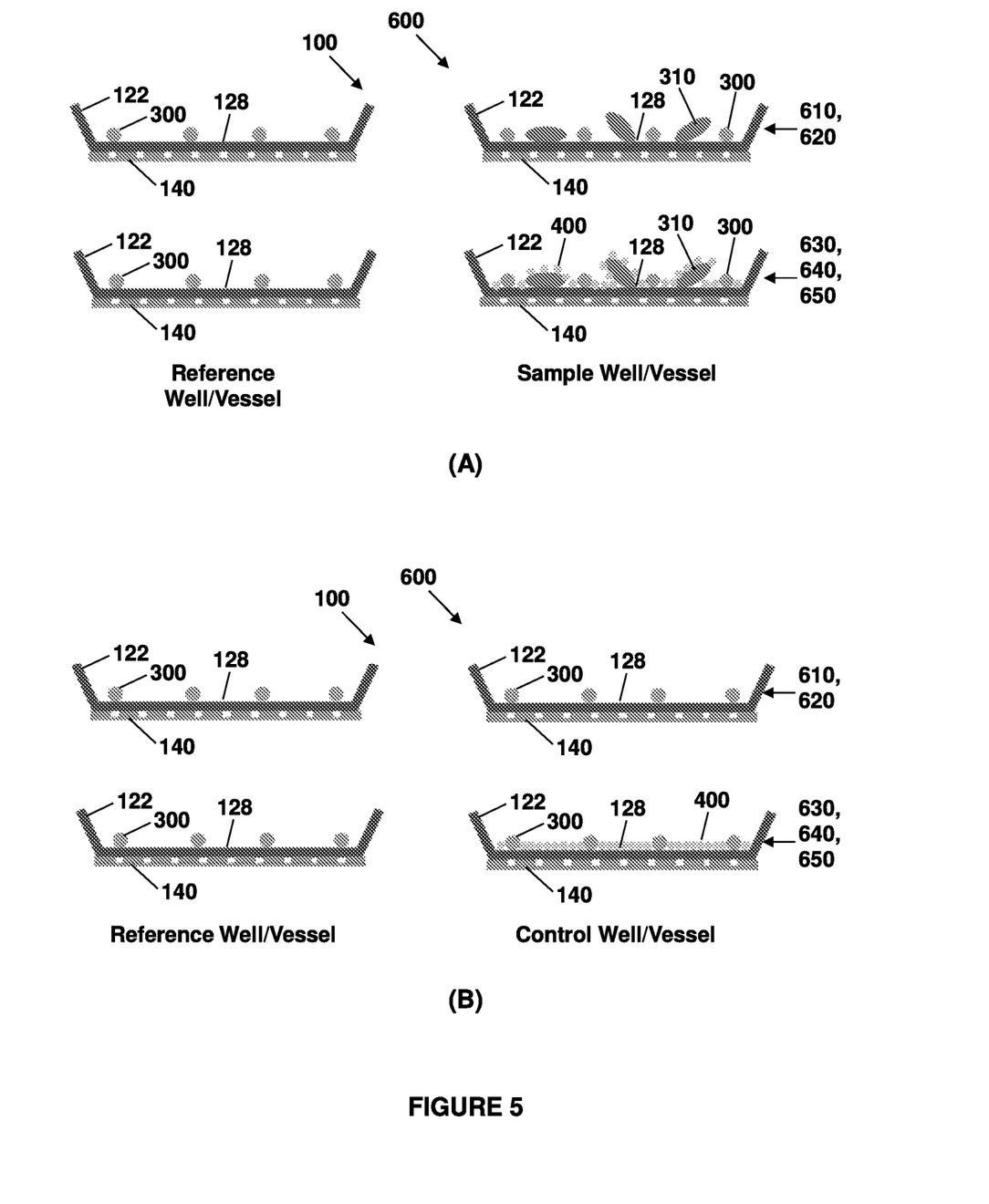
FIG. 5 illustrates methods for detection of a labeled analyte in a sample according to the disclosure. Panel A illustrates the method when the sample includes the target analyte. Panel B illustrates the method when the sample does not include the target analyte, such as for a control sample or a pathogen-free sample.

FIGS. 1 and 5 further illustrate a method 600 for wireless, non-specific detection of electrically, dielectrically, or magnetically labeled analytes 310 using the detection apparatus 100.

In a first step 610, a sample 300 containing or suspected of containing the analyte 310 is added to the internal sample volume 124 of the vessel 120. The sample 300 is not particularly limited, but it can generally include a food item to be tested to evaluate whether the food is safe or otherwise suitable for human or other animal consumption. In a particular embodiment, the sample is milk (e.g., cow's milk), for example combined from multiple different animals. Other types of possible sample materials include water (e.g., bottled water, drinking water), fruit and vegetable juices, energy/soft drinks, other beverages, oils (e.g., cooking oils such as vegetable oils, olive oils), buttermilk or yogurt, meats, etc. Solid or semi-solid materials to be tested can be diluted, extracted, or otherwise contacted with water or other liquid medium before addition to the sample volume 124.

In a further step 620, the sample 300 is incubated for a time sufficient to non-specifically bind at least some of any analyte 310 present in the sample 300 to the wall 122 of the vessel 120. Incubation of the sample 300 to non-specifically bind analyte 310 present in the sample 300 to the wall 122 can include binding due to one or more of electrostatic forces, ionic interactions, hydrogen bonding interactions, and other dipole-dipole interactions. Alternatively or additionally, incubation of the sample 300 can specifically bind analyte 310 present in the sample 310 to wall-immobilized specific-binding members 160 such as antibody and DNA or other oligonucleotide probes. The incubation time for non-specific and/or specific binding can be any suitable time such as 1 to 240 minutes, for example about 30 minutes, and the incubation temperature can be any suitable temperature such as 10 to 80° C., for example about room temperature or 20-30° C. After incubating the sample 300, remaining sample or fluid in the internal sample volume 124 of the vessel 120 can be drained or otherwise removed therefrom, thus leaving analyte 310 originally present in the sample 300 bound to the vessel wall 122. This can include washing of the sample volume 124 with a suitable wash/rinse solution.

In a further step 630, the capped nanoparticle label 400 is added to the internal sample volume 124 of the vessel 120. The capped nanoparticle label 400 includes a nanoparticle (core) 410 and capping agent 420 on an outer surface of the nanoparticles 410. The nanoparticles 410 can be high dielectric constant nanoparticles, electrically conductive nanoparticles, and/or magnetic nanoparticles. Electrically conductive nanoparticles can be formed from or otherwise include one or more metals such as gold, chromium, copper, zinc, nickel, cadmium, silver, cobalt, indium, germanium, tin, lead, arsenic, antimony, bismuth, chromium, molybdenum, manganese, iron, ruthenium, rhodium, palladium, osmium, iridium, platinum, alloys thereof, and combinations thereof. Magnetic nanoparticles can be formed from or otherwise include one or more of a metal or metal oxide including iron, cobalt, nickel, gadolinium, alloys thereof, and combinations thereof. Examples include iron or iron-containing alloy magnetic materials, nickel or nickel-containing alloy magnetic materials, and magnetic iron oxides such as $Fe_3O_4$ or gamma $Fe_2O_3$. High dielectric constant nanoparticles can be formed from or otherwise include conjugated polymers (e.g., conductive polymers), titanium oxides, microwave ferrite materials, and combinations thereof. The capping agent 420 suitably includes a carbohydrate, citric acid, and/or a citric acid derivative (e.g., citrate). In an embodiment, the capping agent includes an oligosaccharide having 3 to 100 saccharide residues, for example dextrin. In a particular embodiment, the capped nanoparticle label 400 includes dextrin-capped 420 gold nanoparticles 410.

In a further step 640, the capped nanoparticle label 400 is incubated for a time sufficient to non-specifically bind the capped nanoparticle label 400 to the vessel wall 122. Incubation of the capped nanoparticle label 400 to non-specifically the capped nanoparticle label 400 to the wall 122 can include binding due to one or more of electrostatic forces, ionic interactions, hydrogen bonding interactions, and other dipole-dipole interactions. The incubation time for non-specific binding can be any suitable time such as 1 to 240 minutes, for example about 30 minutes, and the incubation temperature can be any suitable temperature such as 10 to 80° C., for example about room temperature or 20-30° C. After incubating the capped nanoparticle label 400, remaining label 400 or suspending fluid in the internal sample volume 124 of the vessel 120 can be drained or otherwise removed therefrom, thus removing unbound capped nanoparticle label 400 from the vessel 120. This can include washing of the sample volume 124 with a suitable wash/rinse solution.

In a further step 650, resonance is induced in the resonant tag 140 with an inductively coupled reader 200 and the corresponding resonance frequency of the resonant tag 140 is measured. More generally, the method can include measurement of one or more of resonance frequency, phase change, change in power (e.g., power consumed by the resonant tag), and/or quality-factor (Q-factor). Such measurements can be used for a qualitative or quantitative determination regarding the presence or absence of the analyte in the original sample, for example based on a shift in resonance frequency between the sample resonance frequency and a reference resonance frequency. Example determinations include: analyte is present in original sample, analyte is absent from original sample, analyte has a particular concentration in original sample, etc. In an embodiment, the inductively coupled reader 200 can be a handheld reader. More generally, the inductively coupled reader 200 can be any conventional device that inductively couples to the sensor tag 140. The reader 200 can accept wireless data and can include a readout display that shows the resonance frequency and phase of the sensor. For example, the reader 200 can be a vector network analyzer, a RFID reader (e.g., an active RFID reader, such as for a passive inductive resonant tag), a magnetic inductive coil (wires), or an impedance analyzer.

The reader 200 determines the resonant frequency and/or the quality factor of the resonant frequency. This measurement can be compared against a background-stored electrical property or against a reference resonant tag 140 which undergoes similar conditions apart from interacting with the nanoparticles 400/410. Thus, in an embodiment, the method for analyte detection can include determining a resonance frequency shift between the resonance frequency measured for the sample 300/analyte 310 and a reference resonance frequency. The reference resonance frequency can be based on a control sample that is of the same type/sample matrix as the unknown sample 300, but which is known to be free of the analyte 310, and which has been otherwise analyzed in the same manner as the unknown sample 310. The method can further include determining that the analyte 310 was not present in the sample 300, for example including qualitative determination of absence, or a quantitative determination that the analyte 310 was not present above a lower level of detection. The method can further include determining that the analyte 310 was present in the sample 300, for example including a qualitative determination of presence, or a quantitative determination that the analyte 310 was present at a particular level or concentration (e.g., example based on a separately analyzed calibration curve).

FIG. 1 further illustrates a kit 500 for wireless, non-specific detection electrically, dielectrically, or magnetically labeled analytes. The kit 500 includes one or more detection apparatus 100, each including a sample vessel 120 and a resonant tag 140 as generally described above. The kit 500 further includes the capped nanoparticle label 400, for example in the form of a (concentrated) aqueous or other liquid suspension of the label 400 nanoparticles as generally described above, which suspension can be added as is to a sample vessel 120 or combined/diluted with other components before addition. The kit 500 can further include the inductively coupled reader 200, thus providing a simple means for data analysis, such as when a measured result is above a known, reference threshold value.

EXAMPLES

The following examples illustrate the disclosed apparatus and methods, but are not intended to limit the scope of any of the claims thereto.

Example 1—Detection Apparatus with LC Tank Resonant Tag

This example illustrates detection apparatus according to the disclosure, in particular a wireless, antibody-free biosensor for rapid detection of pathogenic bacteria in milk using dextrin-capped gold nanoparticles (d-AuNP) as markers or labels. The apparatus includes (1) an interdigitated capacitor coupled to an inductor forming an inductor-capacitor (LC) resonant tank as a resonant tag; (2) a detection vessel or vial onto which *E. coli* C3000 suspended in milk matrix, adheres and are labeled with d-AuNP markers; and (3) a wireless pick up coil as a reader. The detection apparatus 100 is schematically illustrated in FIG. 1 and the resonant tag 140 is illustrated in FIG. 2. The surface charge chemistry allows the bacteria in the contaminated milk to attach to the wall of the detection vessel. The bacteria are labeled with d-AuNP markers for detection. Detection is based on impedance loading of the interdigitated sensor by d-AuNP bound to the pathogenic bacteria. The detection vessel includes the interdigitated capacitor coupled to an inductor coil on an external vessel surface. The interdigitated capacitor has strong electric fields in between the fingers, enabling change in capacitance due to d-AuNP loading of the sensor. This capacitive loading shifts the resonance frequency and this shift is correlated to the threshold level of bacteria or other pathogens in the contaminated milk. Resonance frequency shift of the LC tank correlates to the concentration of *E. coli* cells or other pathogens in the milk sample matrix, with the detection apparatus being field-operable and able to detect bacteria counts as low as log 5 CFU/ml within an hour total analysis time (e.g., including two application and incubation periods for the sample followed by the markers, together followed by resonance induction/detection). The resonance frequency of the sensor can be selected to match existing RFID frequency bands or other desired frequencies. The apparatus can detect of a variety of pathogenic bacteria for quality control along a liquid food (e.g., milk) supply chain.

Resonant Tag: FIG. 2 illustrates the resonant tag 140 used in the example. The tag 140 is an RFID-compatible sensor tag including an interdigitated capacitor 144 (C) coupled to an inductor 142 (L) and an external pick-up coil. The substrate chosen for this sensor design was Roger's 3003 high frequency laminate with dielectric constant ($\varepsilon_r$) of 3, loss tangent (tan $\delta$) of 0.0013, and a thickness of 1.52 mm. Suitable physical dimensions of the tag 140 are shown in FIG. 2. The interdigitated capacitor consists of 78 fingers with spacing of 40 μm between the fingers. An inductor coil of 100 pH is soldered onto the pads of the interdigitated capacitor to form an LC resonant tank, and the inductor coil further serves as wireless interface to the external pick-up coil. The measured frequency of operation of the LC tank is at 4.94 MHz. The resonant tag has a high 0-factor which allows for ease of detection of any change in resonant frequency.

Figure 4:
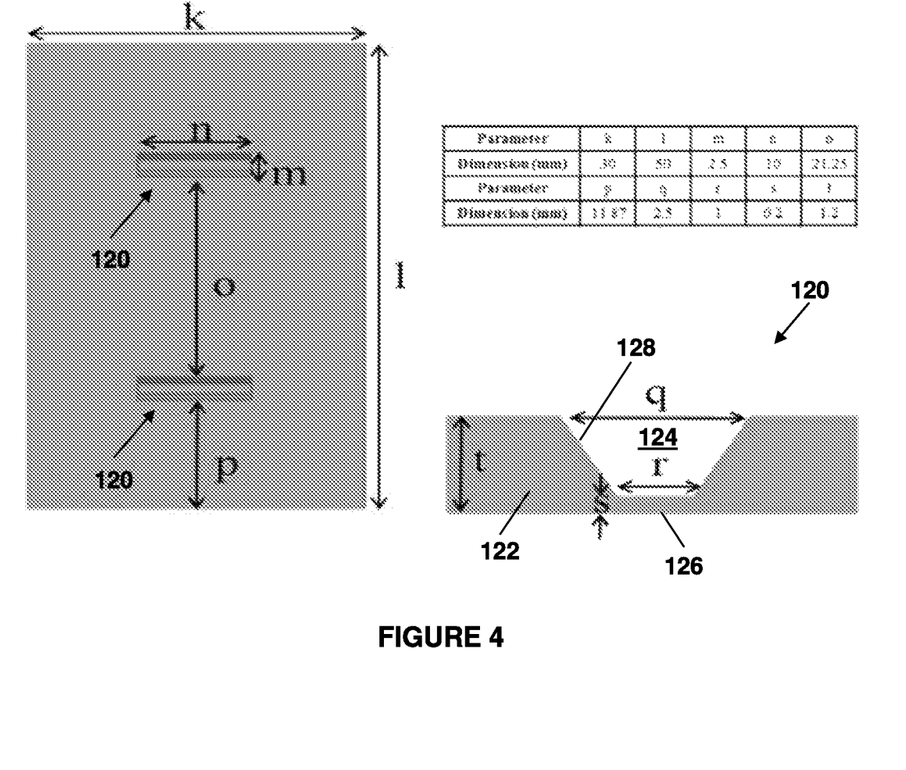
FIG. 4 illustrates detection vessels according to the disclosure in the form of sample vials or wells in a substrate (left: top view; right: side view).

Detection Vessel or Vial: FIG. 4 illustrates the detection vessel or vial 120 used in the example. A flat form was fabricated using 3D printing, with each form having two vessels 120, which can serve as a sample well and a reference well, each with a 20 μL volume. The forms were printed using an acrylic polymer (VEROWHITEPLUS) with a dielectric constant of ~2.8. Suitable physical dimensions of the forms are shown in FIG. 4. The acrylic polymer has negatively charged carboxylic or carbonyl (C=O) groups its surface making the thermoplastic hydrophobic and suitable for non-specific binding or attachment of bacteria or other microbes thereto.

Dextrin-Capped Gold Nanoparticles: Dextrin-capped gold nanoparticle labels 400 (d-AuNP) including a gold nanoparticle core 410 and a dextrin capping agent 420 on the outer surface of the core 410 were formed as described in U.S. Pub. No. 2014/0322823, incorporated herein by reference. A concentrated d-AuNP suspension was prepared by sonicating 75 μL of the as-formed suspension of d-AuNP for 10 min followed by centrifugation at 15,000 rpm at 4° C. for 20 min, followed by supernatant removal and re-sonication/re-suspension of the concentrated d-AuNP. The suspensions were stored at 4° C. and used within 24 hours of preparation. The dextrin carbohydrate capping agent has electronegative or negatively charged hydroxyl (—OH) groups on the surface. The AuNP have a positively charged surface, leading to an electrostatic bond between the dextrin and AuNP in the d-AuNP. Bacteria have a negatively charged cell surface with numerous molecular structures projecting out such as flagella, fimbriae and curli, which assist in surface adhesion and attachment to other cells. The hydroxyl groups of the dextrin may bind to positively charged amino acid pockets within the cellular surface molecules of bacteria, leading to attachment of d-AuNP on the bacterial surface, for example as observed by transmission emission microscopy (TEM) for E. coli. The acrylic surface of the polymeric detection vessel 120 contains electron-rich oxygen atoms with carbonyl (C=O) groups. Binding of d-AuNP to the vessel 120 internal surface 128 was observed using scanning electron microscopy (SEM). Dextrin's hydroxyl groups on d-AuNP may be repulsed by the exposed oxygen atoms of the vessel 120 surface, which repulsion force can result in displacement of dextrin from the d-AuNP, exposing the electrostatic binding of the oxygen atoms to the AuNP surface and leading to binding of AuNP to the oxygen atoms of the vessel 120 surface.

Analytical Sample: Milk was used as the sample 300, and it was contaminated with E. coli as the target analyte 310. Colonies of E. coli C3000 strain from frozen (−70° C.) culture were grown on tryptic soy agar (TSA), a single colony was isolated and inoculated into tryptic soy broth (TSB, Sigma-Aldrich, St. Louis, Mo.) and grown overnight at 37° C., and then a tenfold-dilution within TSB was made and grown for 4 hr. Tenfold dilutions of the culture were made within commercially available Vitamin D milk to form the sample 300/analyte 310 mixture, and a standard plate count was performed to estimate the concentration of bacteria suspended in the milk.

Sample Analysis: FIG. 5 illustrates a method 600 for detecting an analyte according to the disclosure and as performed in this example using a detection apparatus 100. The first step 610 involves filling the sample well (or internal 124 sample volume) with 20 µL of milk spiked with E. coli C3000 as the sample 300/analyte 310 mixture. The cells were allowed to attach to the sample well internal wall 122 for 30 min in an incubation step 620, followed by 500 µL PBS rinse. The next step 630 was to apply the concentrated d-AuNP to the same sample well and allow attachment to the internal wall 122 for 30 min in an incubation step 630, followed by a 500 µL PBS rinse. In parallel, the reference well was filled with 20 µL of non-contaminated milk and allowed to attach/incubate for 30 min, followed by a 500 µL PBS rinse. This series of steps is illustrated in FIG. 5, panel A. The negative control forms were prepared by similar two-step process, but without the presence of bacterial cells in the control well as illustrated in FIG. 5, panel B. A Vector Network Analyzer (VNA, E5070B) and an external pick-up wire coil with a cut off frequency higher than the resonance frequency of the sensor were used to analyze the performance of the sensor tag. The sensor tag was placed in the near-field region of the pick-up coil and the scattering parameters (s-parameters) were averaged 50 times. The resonance frequency shift of the LC tank is directly correlated with the number of d-AuNP that capacitively loads the strong electric field regions of the interdigitated capacitor. As the concentration of E. coli increases, a lower number of d-AuNP bind to the surface of the vessel 120 internal wall 122, leading to lower shift in resonance frequency. Hence, an inverse relationship exists between target analyte concentration and resonance frequency shift due to capacitive loading with conductive nanoparticles.

Results: A set of experiments was performed to demonstrate the ability of the detection apparatus 100 to detect approximately 5 log CFU/ml E. coli C3000 cells in milk. The samples (N=6) and negative controls (N=6) have a concentrated d-AuNP suspension applied to the lower wells. Each form is measured three times for resonance frequency shift of the attached d-AuNP, and the results are averaged. There is a clear distinction between the presence and absence of E. coli C3000 cells, demonstrating the effectiveness of the apparatus 100.

Example 2—Detection Apparatus with Split Ring Resonator Tag

Rapid detection techniques of pathogenic bacteria in the liquid food supply chain are of significant research interest due to their pivotal role in preventing foodborne outbreaks, and in maintaining high standards of public health and safety. Milk and dairy products are of particular interest due to their widespread consumption across the globe. This example illustrates detection apparatus according to the disclosure, in particular a wireless, antibody-free biosensor for rapid detection of pathogenic bacteria in milk using dextrin-capped gold nanoparticles (d-AuNP) as markers or labels. In particular, the biosensor uses d-AuNP as labels decoded at microwave frequencies. The biosensor consists of a 3D printed detection vessel or vial and uses an RF reader and an RFID (radio-frequency identification) compatible split ring resonator (SRR) based tag. The biosensor is capable of detecting bacteria at log 5 CFU/ml within 75 min, with the possibility of testing multiple concurrent samples. Detection is based on impedance loading of SRR by d-AuNP bound to pathogenic bacteria.

Resonant Tag: FIG. 3 illustrates the split ring resonant (SRR) tag 140 used in the example. The tag 140 consists of two square split rings 146 capacitively coupled to a transmission line 148, one ring 146 used for measurement and the other ring 146 for reference. The substrate chosen for this sensor design was Roger's 3003 high frequency laminate with dielectric constant ($\varepsilon_r$) of 3, loss tangent (tan δ) of 0.0013, and a thickness of 1.52 mm. Suitable physical dimensions of the tag 140 are shown in FIG. 3. The SRR is measured using a vector network analyzer (VNA) and the resonance frequency of the first ring was at 3.4 GHz and second at 4.8 GHz. Since the first ring has higher Q-factor than the second one, it was chosen as the measurement ring for all experiments. Detection of a small change in the number of d-AuNP present is achieved by creating strong electric fields in the gap region of the SRR sensor. The d-AuNP perturb the E-field in the gap region and thereby shift the resonance frequency of the SRR.

Detection Vessel or Vial: FIG. 4 illustrates the detection vessel or vial 120 used in the example, which was formed as described in Example 1 above.

Dextrin-Capped Gold Nanoparticles: Dextrin-capped gold nanoparticle labels 400 (d-AuNP) including a gold nanoparticle core 410 and a dextrin capping agent 420 on the outer surface of the core 410 were formed as described in Example 1 above.

Analytical Sample: Milk was used as the sample 300, and it was contaminated with E. coli as the target analyte 310. The sample 300/analyte 310 mixture was formed as described in Example 1 above.

Sample Analysis: Contaminated sample 300/analyte 310 mixtures as well negative sample 300 controls were added to the detection apparatus 100 as described above in Example 1. Subsequent incubation steps and addition of concentrated d-AuNP were also performed as in Example 1. All samples and negative controls were tested for frequency shift along the well, normalized with respect to their reference well, and the values averaged per form (n=3). RF frequency shift results demonstrated significantly lower responses for samples with approximately 5.1 log CFU/mL E. coli C3000, thus discriminating against higher negative control levels.

The inverse signaling relationship is the result of less d-AuNP present in the samples causing a lower shift in the RF frequency.

Because other modifications and changes varied to fit particular operating requirements and environments will be apparent to those skilled in the art, the disclosure is not considered limited to the example chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

All patents, patent applications, government publications, government regulations, and literature references cited in this specification are hereby incorporated herein by reference in their entirety. In case of conflict, the present description, including definitions, will control.

Throughout the specification, where the apparatus, compounds, compositions, methods, and processes are described as including components, steps, or materials, it is contemplated that the compositions, processes, or apparatus can also comprise, consist essentially of, or consist of, any combination of the recited components or materials, unless described otherwise. Component concentrations can be expressed in terms of weight concentrations, unless specifically indicated otherwise. Combinations of components are contemplated to include homogeneous and/or heterogeneous mixtures, as would be understood by a person of ordinary skill in the art in view of the foregoing disclosure.

PARTS LIST 100 detection apparatus
120 vessel
122 vessel wall
124 internal sample volume
126 external surface of vessel/vessel wall
128 internal surface of vessel/vessel wall
140 resonant tag
142 inductor (L)
144 (interdigitated) capacitor (C)
146 split ring
148 transmission line
160 immobilized specific binding member
200 inductively coupled reader
210 RF field for inducing resonance in tag
300 sample
310 target analyte
400 capped nanoparticle label
410 nanoparticle
420 capping agent
500 kit
600 method for analyte detection
610 adding sample (e.g., with or without analyte)
620 incubating sample
630 adding capped nanoparticle label
640 incubating capped nanoparticle label
650 inducing resonance the resonant tag

What is claimed is:

1. A method for wireless, non-specific detection of electrically, dielectrically, or magnetically labeled analytes, the method comprising:
   providing a detection apparatus comprising:
      a vessel comprising a wall defining an internal sample volume, an internal surface, and an opposing external surface, wherein (i) the internal sample volume is adapted to receive a sample containing or suspected of containing an analyte selected from the group consisting of bacteria, viruses, and combinations thereof, and (ii) the internal surface of the wall is adapted to non-specifically bind with both the analyte and a capped nanoparticle label; and
      a resonant tag, positioned at the external surface of the vessel at a location opposing the internal surface of the wall adapted to non-specifically bind with both the analyte and the capped nanoparticle label, wherein the resonant tag is adapted to (i) wirelessly receive an induced voltage from an inductively coupled reader, and (ii) correspondingly resonate at a selected resonance frequency in the absence of an additional capacitive load; and
   adding a sample containing or suspected of containing the analyte to the internal sample volume of the vessel;
   incubating the sample for a time sufficient to non-specifically bind analyte present in the sample to the internal surface of the wall of the vessel;
   after incubating the sample, removing the sample from the internal sample volume of the vessel, leaving analyte originally present in the sample still in the internal sample volume of the vessel and bound to the internal surface of the wall of the vessel;
   adding a capped nanoparticle label to the internal sample volume of the vessel, the capped nanoparticle label comprising: (i) one or more of high dielectric constant nanoparticles, electrically conductive nanoparticles, and magnetic nanoparticles, and (ii) a capping agent on an outer surface of the nanoparticles;
   incubating the capped nanoparticle label for a time sufficient to non-specifically bind the capped nanoparticle label [i] to the internal surface of the wall of the vessel and (ii) analyte bound to the internal surface of the wall of the vessel;
   after incubating the capped nanoparticle label, removing unbound capped nanoparticle label from the internal sample volume of the vessel; and
   inducing resonance in the resonant tag with an inductively coupled reader and measuring the corresponding resonance frequency of the resonant tag.

2. The method of claim 1, wherein the wall of the vessel comprises a material selected from the group consisting of a polymer plastic, ceramic, and glass.

3. The method of claim 1, wherein the wall of the vessel comprises a polymer selected from the group consisting of acrylics, polycarbonates, polyamides, polystyrenes, polyolefins, polyvinylchlorides, polyesters, polyurethanes, poly (acrylonitrile butadiene styrene) (ABS), copolymers thereof, and combinations thereof.

4. The method of claim 1, wherein the wall of the vessel has a thickness in a range from 0.025 mm to 10 mm.

5. The method of claim 1, wherein the internal sample volume is in a range from 0.005 ml to 1000 ml.

6. The method of claim 1, wherein the vessel is in the form of a sealable container, and the resonant tag is mounted at an external surface of the sealable container.

7. The method of claim 1, wherein the resonant tag comprises an LC tank.

8. The method of claim 7, wherein the LC tank comprises an interdigitated capacitor element.

9. The method of claim 1, wherein the resonant tag comprises a radio-frequency identification (RFID) tag.

10. The method of claim 1, wherein the selected resonance frequency of the inductive resonant tag is in a range from 1 MHz to 20 MHz.

11. The method of claim 1, wherein the sample comprises milk.

12. The method of claim 1, wherein the analyte comprises bacteria.

13. The method of claim 1, wherein the capped nanoparticle label comprises electrically conductive nanoparticles.

14. The method of claim 13, wherein the electrically conductive nanoparticles comprise a metal selected from the group consisting of gold, chromium, copper, zinc, nickel, cadmium, silver, cobalt, indium, germanium, tin, lead, arsenic, antimony, bismuth, chromium, molybdenum, manganese, iron, ruthenium, rhodium, palladium, osmium, iridium, platinum, alloys thereof, and combinations thereof.

15. The method of claim 1, wherein the capped nanoparticle label comprises magnetic nanoparticles.

16. The method of claim 15, wherein the magnetic nanoparticles comprise a metal or metal oxide selected from the group consisting of iron, cobalt, nickel, gadolinium, alloys thereof, and combinations thereof.

17. The method of claim 1, wherein the capped nanoparticle label comprises high dielectric constant nanoparticles.

18. The method of claim 17, wherein the high dielectric constant nanoparticles comprise a material selected from the group consisting of conjugated polymers, titanium oxides, microwave ferrite materials, alumina, ceria, and combinations thereof.

19. The method of claim 1, wherein the nanoparticles have a particle size ranging from 2 nm to 250 nm.

20. The method of claim 1, wherein the capping agent comprises at least one of a carbohydrate, citric acid, and a citric acid derivative.

21. The method of claim 1, wherein the capping agent comprises an oligosaccharide having 3 to 100 saccharide residues.

22. The method of claim 1, wherein the capped nanoparticle label comprises gold nanoparticles and a dextrin capping agent.

23. The method of claim 1, wherein the inductively coupled reader is a handheld reader.

24. The method of claim 1, further comprising: determining a resonance frequency shift between the resonance frequency measured for the sample and a reference resonance frequency.

25. The method of claim 24, further comprising: determining that the analyte was not present in the sample.

26. The method of claim 24, further comprising: determining that the analyte was present in the sample.

27. The method of claim 24, further comprising: determining whether the analyte was present in the sample.

28. A method for supply chain safety management of a product, the method comprising:
taking a sample of a product to be analyzed for the presence of an analyte;
performing the method of claim 27 to determine whether the analyte was present in the sample;
combining the product with a bulk supply of other corresponding product, depending on whether the analyte was present in the sample.

29. The method of claim 1, wherein:
the analyte is selected from the group consisting of bacteria;
the wall of the vessel comprises a material selected from the group consisting of a polymer plastic, ceramic, and glass;
the capping agent comprises at least one of a carbohydrate, citric acid, and a citric acid derivative;
non-specific binding between the internal surface of the wall of the vessel and the analyte present in the sample is due to one or more of electrostatic forces, ionic interactions, hydrogen bonding, and dipole-dipole interactions;
non-specific binding between the internal surface of the wall of the vessel and the capped nanoparticle label is due to one or more of electrostatic forces, ionic interactions, hydrogen bonding, and dipole-dipole interactions; and
non-specific binding between the analyte bound to the internal surface of the wall of the vessel and the capped nanoparticle label is due to one or more of electrostatic forces, ionic interactions, hydrogen bonding, and dipole-dipole interactions.

30. The method of claim 1, wherein:
the analyte is selected from the group consisting of bacteria;
the wall of the vessel comprises a polymer plastic;
the capping agent comprises an oligosaccharide having 3 to 100 saccharide residues;
non-specific binding between the internal surface of the wall of the vessel and the analyte present in the sample is due to one or more of electrostatic forces, ionic interactions, and hydrogen bonding;
non-specific binding between the internal surface of the wall of the vessel and the capped nanoparticle label is due to one or more of electrostatic forces, ionic interactions, and hydrogen bonding; and
non-specific binding between the analyte bound to the internal surface of the wall of the vessel and the capped nanoparticle label is due to one or more of electrostatic forces, ionic interactions, and hydrogen bonding.

31. The method claim 30, wherein:
the polymer plastic comprises one or more functional groups selected from the group consisting of carbonyl groups, carboxylic acid groups, carboxylate groups, hydroxyl groups, amino groups, ester groups, amide groups, and combinations thereof;
the capping agent comprises dextrin;
non-specific binding between the internal surface of the wall of the vessel and the analyte present in the sample is due at least to electrostatic forces;
non-specific binding between the internal surface of the wall of the vessel and the capped nanoparticle label is due at least to electrostatic forces; and
non-specific binding between the analyte bound to the internal surface of the wall of the vessel and the capped nanoparticle label is due at least to electrostatic forces.

* * * * *